(12) United States Patent
Kikugawa et al.

(10) Patent No.: US 9,526,246 B2
(45) Date of Patent: Dec. 27, 2016

(54) HERBICIDAL COMPOSITION HAVING IMPROVED HERBICIDAL ACTIVITY

(71) Applicant: ISHIHARA SANGYO KAISHA, LTD., Osaka (JP)

(72) Inventors: Hiroshi Kikugawa, Osaka (JP); Ryu Yamada, Shiga (JP); Mitsuru Endo, Mie (JP); Yoshikazu Satake, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 14/410,354

(22) PCT Filed: Jun. 27, 2013

(86) PCT No.: PCT/JP2013/068307
§ 371 (c)(1),
(2) Date: Dec. 22, 2014

(87) PCT Pub. No.: WO2014/003202
PCT Pub. Date: Jan. 3, 2014

(65) Prior Publication Data
US 2015/0216165 A1 Aug. 6, 2015

(30) Foreign Application Priority Data
Jun. 29, 2012 (JP) .................. 2012-147798

(51) Int. Cl.
| | |
|---|---|
| A01N 43/56 | (2006.01) |
| A01N 25/30 | (2006.01) |
| A01N 37/36 | (2006.01) |
| A01N 47/06 | (2006.01) |
| A01N 43/08 | (2006.01) |
| A01N 25/04 | (2006.01) |

(52) U.S. Cl.
CPC .............. *A01N 43/56* (2013.01); *A01N 25/30* (2013.01); *A01N 37/36* (2013.01); *A01N 43/08* (2013.01); *A01N 47/06* (2013.01)

(58) Field of Classification Search
CPC ........ A01N 43/56; A01N 37/36; A01N 47/06; A01N 43/08; A01N 25/30
See application file for complete search history.

(56) References Cited

U.S. PATENT DOCUMENTS

| | | |
|---|---|---|
| 6,831,039 B1 | 12/2004 | Neidlein et al. |
| 7,112,554 B2 | 9/2006 | Herrmann et al. |
| 7,456,133 B2 | 11/2008 | Herrmann et al. |
| 2002/0016262 A1 | 2/2002 | Nakamura et al. |
| 2003/0220199 A1 | 11/2003 | Nakamura et al. |
| 2004/0162221 A1 | 8/2004 | Nakamura et al. |
| 2004/0176253 A1 | 9/2004 | Hermann et al. |
| 2006/0252647 A1 | 11/2006 | Herrmann et al. |
| 2009/0286683 A1 | 11/2009 | Shimoharada et al. |
| 2010/0075855 A1 | 3/2010 | Komyoji et al. |
| 2010/0197500 A1 | 8/2010 | Kikugawa et al. |
| 2010/0317528 A1 | 12/2010 | Shimoharada et al. |
| 2011/0160062 A1 | 6/2011 | Tsukamoto et al. |
| 2011/0282070 A1 | 11/2011 | Shimoharada et al. |

FOREIGN PATENT DOCUMENTS

| | | |
|---|---|---|
| EP | 2103215 | 9/2009 |
| EP | 2172104 | 4/2010 |
| JP | 2001-151613 | 6/2001 |
| WO | 00/34273 | 6/2000 |
| WO | 02/090336 | 11/2002 |
| WO | 2007/069771 | 6/2007 |
| WO | 2008/065907 | 6/2008 |
| WO | 2008/078811 | 7/2008 |
| WO | 2009/011321 | 1/2009 |
| WO | 2009/142318 | 11/2009 |

OTHER PUBLICATIONS

Kubota, T, Herbicidal Composition Comprising Substituted Benzoyl Compounds and/or their salts and Nonionic Surfactants is Useful for Weed Control in Maize or other Crop Fields, 2001, Derwent Abstract of JP 2001151613, 4 pages.*
International Search Report and written opinion in respect to International Application No. PCT/JP2013/068307, dated Aug. 26, 2013.
International Preliminary Report on Patentability in respect to International Application No. PCT/JP2013/068307, dated Jan. 8, 2015.
Costa Rican Notice of Opposition with English Translation in respect to Costa Rican Application No. 2014-0579, dated Jun. 19, 2015.

* cited by examiner

*Primary Examiner* — John Pak
*Assistant Examiner* — Andriae M Holt
(74) *Attorney, Agent, or Firm* — Greenblum & Bernstein, P.L.C.

(57) ABSTRACT

In order to reduce the environmental load on an area where a herbicide is applied or a surrounding area thereof more than ever, it has been required to improve activity of a herbicidal active ingredient and to reduce its dose as far as possible.
A herbicidal composition comprising (1) a benzoylpyrazole compound represented by the formula (I) or its salt:

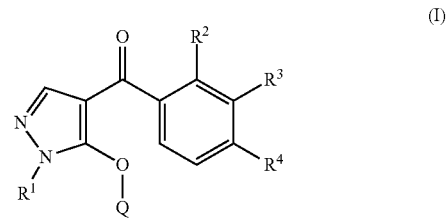

wherein each of Q, $R^1$, $R^2$, $R^3$, $R^4$, $R^5$, $R^6$ and A is as defined in the specification, and (2) at least one compound selected from the group consisting of a polyoxyalkylene sorbitan fatty acid ester, a polyoxyalkylene fatty acid ester, a polyoxyalkylene styryl aryl ether, a polyoxyalkylene styryl aryl ether condensate and a polyoxyalkylene alkyl ether sulfate.

9 Claims, No Drawings

HERBICIDAL COMPOSITION HAVING IMPROVED HERBICIDAL ACTIVITY

TECHNICAL FIELD

The present invention relates to a herbicidal composition having improved herbicidal activity.

BACKGROUND ART

Heretofore, in cultivation of crop plants in cropland, it has been desired to control weeds which inhibit the growth or the harvest of crop plants. Further, in non-cropland also, it is beneficial for utilization of the non-cropland to effectively control weeds. Thus, control of weeds is necessary in each of cropland and non-cropland, and various herbicides have been used. However, in recent years, there is a movement to reduce the dosage of a herbicidal active ingredient as far as possible, so as to reduce the environmental load on an area where the herbicide is applied or a surrounding area thereof. For example, certain herbicidal benzoylpyrazole compounds have been known (Patent Documents 1 to 4), and a herbicidal composition comprising a compound including such herbicidal benzoylpyrazole compounds and a polyoxyalkylene alkyl ether phosphate or its salt has been known (Patent Document 5).

PRIOR ART DOCUMENTS

Patent Documents

Patent Document 1: WO2007/069771
Patent Document 2: WO2008/065907
Patent Document 3: WO2008/078811
Patent Document 4: WO2009/142318
Patent Document 5: WO2009/011321

DISCLOSURE OF INVENTION

Technical Problem

It has been desired to improve activity of a herbicidal active ingredient and to reduce the dosage as far as possible, in order to reduce the environmental load on an area where the herbicide is applied or a surrounding area thereof, more than ever.

Solution to Problem

The present inventors have conducted extensive studies to accomplish the above object and as a result, have found that herbicidal activity of the compound represented by the following formula (I) or its salt can be remarkably improved by using a specific compound, and accomplished the present invention.

That is, the present invention relates to a herbicidal composition comprising (1) a benzoylpyrazole compound represented by the formula (I) or its salt (hereinafter referred to as a herbicidal benzoylpyrazole compound):

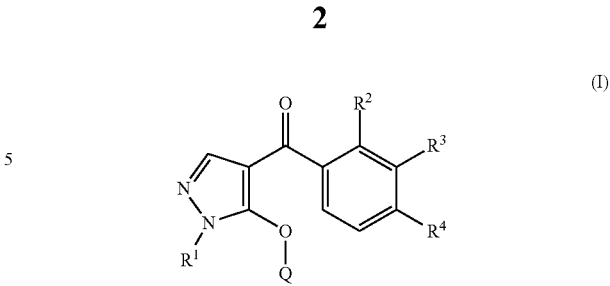

wherein Q is a hydrogen atom, —C(O)SR$^5$ or -A-O—C(O)OR$^6$; R$^1$ is alkyl; R$^2$ is alkyl; R$^3$ is alkoxyalkoxy; R$^4$ is alkylsulfonyl; R$^5$ is alkyl; R$^6$ is alkyl; and A is alkylene substituted by one or more alkyl groups, and (2) at least one compound selected from the group consisting of a polyoxyalkylene sorbitan fatty acid ester, a polyoxyalkylene fatty acid ester, a polyoxyalkylene styryl aryl ether, a polyoxyalkylene styryl aryl ether condensate and a polyoxyalkylene alkyl ether sulfate (hereinafter referred to as an activity-improving component). The present invention further relates to a method for controlling undesired plants, which comprises applying a herbicidally effective amount of the herbicidal benzoylpyrazole compound and an amount effective for activity improvement of the activity-improving component, to the undesired plants or to a place where they grow. The present invention further relates to a method for improving herbicidal activity of the herbicidal benzoylpyrazole compound by the activity-improving component.

In a case of an active ingredient which is taken in the plant body to exhibit herbicidal effect, such as the above herbicidal benzoylpyrazole compound, an improvement in the permeability of plant cuticles is presumed to be effective to obtain higher herbicidal effect. An oil-based adjuvant such as a fatty acid has been known to improve the permeability of plants, however, it is not necessarily sufficient to improve the herbicidal effect of the herbicidal benzoylpyrazole compound. Whereas, an adjuvant which improves the spreading of the herbicidal component on plants (for example, on leaves), i.e. wettability, has been known, however, it also cannot achieve a sufficient improvement in the herbicidal activity. The present inventors have found that the herbicidal effect of the herbicidal benzoylpyrazole compound is remarkably improved by using a specific adjuvant which improves both of the above permeability and wettability. Further, although an improvement in both of the permeability and the wettability may sometimes promote phytotoxicity against crop plants, in the present invention, such a problem does not arise, and practically excellent performance can be achieved.

Advantageous Effects of Invention

According to the present invention, the herbicidal activity of the herbicidal benzoylpyrazole compound is effectively brought about and improved by the activity-improving component. Further, the dosage of the herbicidal benzoylpyrazole compound can be reduced, and the environmental load on an area where the herbicide is applied or a surrounding area thereof can remarkably be reduced. Further, the reduction in the dosage of the herbicidal benzoylpyrazole compound can remarkably reduce the cost required for storage and carrying of a composition containing it.

DESCRIPTION OF EMBODIMENTS

The present invention is carried out, for example, in such a manner that the herbicidal benzoylpyrazole compound is formulated by using various additives, and the formulation is diluted with e.g. water together with the activity-improving component and applied to undesired plants or to a place where they grow. Further, the present invention is carried out in such a manner that the herbicidal benzoylpyrazole compound and the activity-improving component are formulated together by using various additives, and the formulation diluted with e.g. water or without being diluted is applied to undesired plants or to a place where they grow.

In the above formula (I), the alkyl or the alkyl moiety has from about 1 to about 6 carbon atoms, may be either linear or branched, and may, for example, be specifically methyl, ethyl, propyl, butyl, tert-butyl, pentyl or hexyl.

As the herbicidal benzoylpyrazole compound, for example, compounds as shown in Table 1 may be mentioned. In Table 1, No. represents the compound number, Me a methyl group, Et an ethyl group and Bu(t) a tertiary butyl group. These compounds are known compound disclosed in WO2007/069771, WO2008/065907, WO2008/078811 or WO2009/142318.

TABLE 1

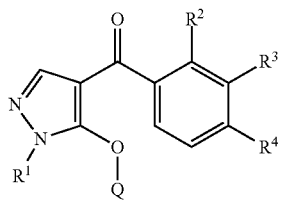

(I)

| No. | Q | $R^1$ | $R^2$ | $R^3$ | $R^4$ |
|---|---|---|---|---|---|
| 1 | H | Me | Me | —O—$(CH_2)_2$—OMe | $SO_2Me$ |
| 2 | H | Et | Me | —O—$(CH_2)_2$—OMe | $SO_2Me$ |
| 3 | —C(O)SEt | Me | Me | —O—$(CH_2)_2$—OMe | $SO_2Me$ |
| 4 | —C(O)SBu(t) | Me | Me | —O—$(CH_2)_2$—OMe | $SO_2Me$ |
| 5 | —CH(Me)—O—C(O)OMe | Me | Me | —O—$(CH_2)_2$—OMe | $SO_2Me$ |
| 6 | —CH(Me)—O—C(O)OMe | Et | Me | —O—$(CH_2)_2$—OMe | $SO_2Me$ |
| 7 | —CH(Me)—O—C(O)OMe | Me | Et | —O—$(CH_2)_2$—OMe | $SO_2Me$ |
| 8 | —CH(Me)—O—C(O)OEt | Me | Me | —O—$(CH_2)_2$—OMe | $SO_2Me$ |
| 9 | —CH(Me)—O—C(O)OEt | Et | Me | —O—$(CH_2)_2$—OMe | $SO_2Me$ |

The salt contained in the herbicidal benzoylpyrazole compound may be any salt so long as it is agriculturally acceptable, and it may, for example, be specifically an alkali metal salt such as a sodium salt or a potassium salt; an alkaline earth metal salt such as a magnesium salt or a calcium salt; an amine salt such as a dimethylamine salt or a triethylamine salt; an inorganic acid salt such as a hydrochloride, a perchlorate, a sulfate or a nitrate; or an organic acid salt such as an acetate or a methanesulfonate.

In a case where the herbicidal benzoylpyrazole compound has various structural isomers such as optical isomers or keto-enol tautomers, such isomers are, of course, included in the present invention.

As at least one compound selected from the group consisting of a polyoxyalkylene sorbitan fatty acid ester, a polyoxyalkylene fatty acid ester, a polyoxyalkylene styryl aryl ether, a polyoxyalkylene styryl aryl ether condensate and a polyoxyalkylene alkyl ether sulfate, which is the activity-improving component, a commercially available surfactant containing the above compound may be used.

In the above respective compounds as the activity-improving component, the number of addition of the oxyalkylene moiety is preferably from about 1 to about 100, more preferably from about 1 to about 50, further preferably from about 1 to about 30, further preferably from about 4 to about 30. Further, the oxyalkylene moiety may be either linear or branched, and it preferably has, for example, from about 2 to about 3 carbon atoms. Specific examples thereof include ethylene oxide, propylene oxide and —$CH(CH_3)CH_2O$—. Hereinafter the polyoxyalkylene moiety may sometimes be referred to as POA and the polyoxyethylene moiety as POE.

In the respective compounds as the activity-improving component, the oxyalkylene moiety may be a copolymer or a block copolymer, and the position of substitution of the oxyalkylene moiety is not particularly limited.

Now, the POA sorbitan fatty acid ester will be described below.

The POA sorbitan fatty acid ester may be any of a mono-fatty acid ester, a di-fatty acid ester and a tri-fatty acid ester.

The fatty acid moiety of the POA sorbitan fatty acid ester may be either a saturated fatty acid or an unsaturated fatty acid. The fatty acid moiety has preferably from about 4 to about 24, more preferably from about 8 to about 20 carbon atoms. The fatty acid moiety may be linear, branched or cyclic, and may have a substituent. The number of the unsaturated bond(s) in the unsaturated fatty acid may be one or more, and the position is also optional. Specific examples of the fatty acid moiety include butyric acid, valeric acid, caproic acid, enanthic acid, caprylic acid, pelargonic acid, capric acid, lauric acid, myristic acid, pentadecylic acid, palmitic acid, palmitoleic acid, margaric acid, stearic acid, oleic acid, vaccenic acid, linoleic acid, (9,12,15)-linolenic acid, tuberculostearic acid, arachidic acid, arachidonic acid, behenic acid, erucic acid, lignoceric acid and nervonic acid.

Specific examples of the POA sorbitan fatty acid ester include the following compounds. Further, tradenames for commercially available surfactants containing the compounds are exemplified. However, the activity-improving component of the present invention is not limited thereto.

[Specific Examples]
POE sorbitan monolaurate
POE sorbitan dilaurate
POE sorbitan trilaurate
POE sorbitan monopalmitate
POE sorbitan dipalmitate
POE sorbitan tripalmitate
POE sorbitan monomyristate
POE sorbitan dimyristate
POE sorbitan trimyristate
POE sorbitan monostearate
POE sorbitan distearate
POE sorbitan tristearate
POE sorbitan monoisostearate
POE sorbitan diisostearate
POE sorbitan triisostearate
POE sorbitan monooleate
POE sorbitan dioleate
POE sorbitan trioleate

[Tradenames]
RHEODOL TW-L120, TW-L106, TW-P120, TW-S120V, TW-S106V, TW-S320V, TW-O120V, TW-O106V and TW-O320V (each manufactured by Kao Corporation)
Sorbon T-20, T-40, T-60, T-80 and T-85 (each manufactured by TOHO Chemical Industry Co., Ltd.)
AGNIQUE SML-20, SMS-20, STS-16, STS-20, SMO-5, SMO-20, SMO-30, STO-20, STO-2095 and STO-2299 (each manufactured by BASF)
NONION LT-221, LT-20, PT-221, OT-206, OT-221, OT-80, ST-206, ST-221, ST-60, LT-210 and IST-221 (each manufactured by NOF CORPORATION)

NIKKOL TL-10, TP-10EX, TS-10V, TS-106V, TS-30V, TI-10, TO-10, TO-106V and TO-30V (each manufactured by NIKKO CHEMICALS CO., LTD.)

The POA fatty acid ester will be described below.

The POA fatty acid ester may be either a mono-fatty acid ester or a di-fatty acid ester.

The fatty acid moiety of the POA fatty acid ester is the same as that of the above-described POA sorbitan fatty acid ester.

Specific examples of the POA fatty acid ester include the following compounds. Further, tradenames for commercially available surfactants containing the compounds are exemplified. However, the activity-improving component of the present invention is not limited thereto.

[Specific Examples]
POE monolaurate
POE dilaurate
POE monooleate
POE dioleate
POE monostearate
POE distearate
POE monoisostearate
POE diisostearate
POE monopalmitate
POE dipalmitate
POE monomyristate
POE dimyristate
POE di-2-ethylhexoate
POE dierucate

[Tradenames]
PEGNOL 24-O, 14-O and EDS(S) (each manufactured by TOHO Chemical Industry Co., Ltd.)

AGNIQUE PEG 200ML, 600ML, 200MO, 260MO, 300MO, 400MO, 600MO, 400MS, 660MS, 300DO, 400DO, 600DO and 200DL (each manufactured by BASF)

CITHROL 4MS, 10MS, 4ML, 6ML, 2DO, 2DE, 4DL and 4DS (each manufactured by CRODA)

NIKKOL MYL-10, MYS-10, MYS-45 and MYO-10 (each manufactured by NIKKO CHEMICALS CO., LTD.)

NONION L-2, L-4, O-2, O-4, O-6, S-1, S-2, S-4, S-6, S-10, S-15, MM-4, MM-9, IS-2, IS-4, IS-6, DL-4HN, DP-1.5HN, DO-4HN, DS-4HN, DIS-400 and DIS-600 (each manufactured by NOF CORPORATION)

ETHOFAT O/15, O/20 and 60/15 (each manufactured by Lion Corporation)

LIONON MO-60, DT-600M, DT-600S and DBH-40 (each manufactured by Lion Corporation)

The POA styryl aryl ether will be described below.

The POA styryl aryl ether may be any of a POA monostyryl aryl ether, a POA distyryl aryl ether and a POA tristyryl aryl ether.

The aryl moiety of the POA styryl aryl ether may, for example, be phenyl.

Specific examples of the POA styryl aryl ether include the following compounds. Further, tradenames for commercially available surfactants containing the compounds are exemplified. However, the activity-improving component of the present invention is not limited thereto.

[Specific Examples]
POE monostyryl phenyl ether
POE distyryl phenyl ether
POE tristyryl phenyl ether

[Tradenames]
Sorpol T-10, T-15, T-20, T-26, T-30, T-32 and T-18D (each manufactured by TOHO Chemical Industry Co., Ltd.)

AGNIQUE TSP-14, TSP-15, TSP-16, TSP-17 and TSP-34 (each manufactured by BASF)

Soprophor BSU, TS/10, TS/16, TS/29, TS/54, CY/8 and S/40 (each manufactured by Rhodia)

Emulsogen TS100, TS160, TS200, TS290, TS400, TS540 and TS600 (each manufactured by Clariant)

The POA styryl aryl ether condensate will be described below. The POA styryl aryl ether condensate is a condensate of a POA styryl aryl ether with formaldehyde.

The POA styryl aryl ether condensate may be any of a POA monostyryl aryl ether condensate, a POA distyryl aryl ether condensate and a POA tristyryl aryl ether condensate, and optional ones among the POA monostyryl aryl ether, the POA distyryl aryl ether and the POA tristyryl aryl ether may be condensed.

The aryl moiety of the POA styryl aryl ether may, for example, be phenyl.

Specific examples of the POA styryl aryl ether condensate include the following compounds. Further, tradenames for commercially available surfactants containing the compounds are exemplified. However, the activity-improving component of the present invention is not limited thereto.

[Specific Examples]
POE monostyryl phenyl ether condensate
POE distyryl phenyl ether condensate
POE tristyryl phenyl ether condensate

[Tradenames]
Sorpol F-15, F-19, F-24 and F-27 (each manufactured by TOHO Chemical Industry Co., Ltd.)

The POA alkyl ether sulfate will be described below.

The alkyl moiety of the POA alkyl ether sulfate preferably has from about 12 to about 14 carbon atoms. The alkyl moiety may be linear, branched or cyclic, and may have a substituent. Specific examples of the alkyl moiety include dodecyl, tridecyl and tetradecyl.

As the salt of the POA alkyl ether sulfate, various salts may be mentioned, such as a sodium salt, a potassium salt, a calcium salt, an ammonium salt and a triethanolamine salt.

Specific examples of the POA alkyl ether sulfate include the following compounds. Further, tradenames for commercially available surfactants containing the compounds are exemplified. However, the activity-improving component of the present invention is not limited thereto.

[Specific Examples]
Ammonium POE lauryl ether sulfate
Ammonium POE dodecyl ether sulfate
Ammonium POE tridecyl ether sulfate
Ammonium POE tetradecyl ether sulfate
Sodium POE lauryl ether sulfate
Sodium POE dodecyl ether sulfate
Sodium POE tridecyl ether sulfate
Sodium POE tetradecyl ether sulfate
Triethanolamine POE lauryl ether sulfate
Triethanolamine POE dodecyl ether sulfate
Triethanolamine POE tridecyl ether sulfate
Triethanolamine POE tetradecyl ether sulfate

[Tradenames]
HITENOL LA12 and LA14 (each manufactured by DAI-ICHI KOGYO SEIYAKU CO., LTD.)

NIKKOL NES-203-27, NES-303-36, SBL-2A-27, SBL-2N-27, SBL-2T-36 and SBL-3N-27 (each manufactured by NIKKO CHEMICALS CO., LTD.)

EMAL 20C, E-27C, 270J, 20CM, D-3-D, D-4-D, 20T, 125HP, 170J and 327 (each manufactured by Kao Corporation)

LATEMUL E-118B, E-150 and WX (each manufactured by Kao Corporation)

PERSOFT EL, EK, EF, EFK and EF-T (each manufactured by NOF CORPORATION)

ALSCOAP TH-330, TH-330K, NS-230, TH-370N, DA-330S, N-355T and A-225B (each manufactured by TOHO Chemical Industry Co., Ltd.)

In the present invention, the mixing ratio of the herbicidal benzoylpyrazole compound to the activity-improving component cannot generally be defined, as it varies depending upon various conditions such as the types of the herbicidal benzoylpyrazole compound and the activity-improving component, the type of the formulation, the weather conditions, and the type and the growth stage of plants to be controlled, and is preferably from 1:0.015 to 1:600, more preferably from 1:0.03 to 1:600, further preferably from 1:0.75 to 1:150, particularly preferably from 1:0.75 to 1:100 by the weight ratio.

The herbicidal composition of the present invention are capable of controlling a wide range of undesired weeds, such as Gramineae such as barnyardgrass (*Echinochloa crus-galli* L., *Echinochloa oryzicola* vasing.), crabgrass (*Digitaria sanguinalis* L., *Digitaria ischaemum* Muhl., *Digitaria adscendens* Henr., *Digitaria microbachne* Henr., *Digitaria horizontalis* Willd.), green foxtail (*Setaria viridis* L.), giant foxtail (*Setaria faberi* Herrm.), yellow foxtail (*Setaria lutescens* Hubb.), goosegrass (*Eleusine indica* L.), wild oat (*Avenal fatwa* L.), johnsongrass (*Sorghum halepense* L.), quackgrass (*Agropyron repens* L.), alexandergrass (*Brachiaria plantaginea*), guineagrass (*Panicum maximum* Jacq.), paragrass (*Panicum purpurascens*), sprangletop (*Leptochloa chinensis*), red sprangletop (*Leptochloa panicea*), annual bluegrass (*Poa annua* L.), black grass (*Alopecurus myosuroides* Huds.), cholorado bluestem (*Agropyron tsukushiense* (Honda) Ohwi), broadleaf signalgrass (*Brachiaria platyphylla* Nash), southern sandbur (*Cenchrus echinatus* L.), italian ryegrass (*Lolium multiflorum* Lam.), and bermudagrass (*Cynodon dactylon* Pers.); Cyperaceae such as rice flatsedge (*Cyperus iria* L.), purple nut sedge (*Cyperus rotundus* L.), yellow nut sedge (*Cyperus esculentus* L.), Japanese bulrush (*Scirpus juncoides*), flatsedge (*Cyperus serotinus*), small-flower umbrellaplant (*Cyperus difformis*), slender spikerush (*Eleocharis acicularis*), and water chestnut (*Eleocharis kuroquwai*); Alismataceae such as Japanese ribbon waparo (*Saqittaria pyqmaea*), arrow-head (*Sagittaria trifolia*), and narrowleaf waterplantain (*Alisma canaliculatum*); Pontederiaceae such as *monochoria* (*Monochoria vaginalis*), and *monochoria* species (*Monochoria korsakowii*); Scrophulariaceae such as false pimpernel (*Lindernia pyxidaria*), and abunome (*Dopatrium junceum*); Lythraceae such as toothcup (*Rotala india*), and red stem (*Ammannia multiflora*); Elatinaceae such as long stem waterwort (*Elatine triandra* SCHK.); Malvaceae such as velvetleaf (*Abutilon theophrasti* MEDIC.), and prickly *sida* (*Sida spinosa* L.); Compositae such as common cocklebur (*Xanthium strumarium* L.), common ragweed (*Ambrosia elatior* L.), thistle (*Breea setosa* (BIEB.) KITAM.), hairy *galinsoga* (*Galinsoga ciliata* Blake), wild chamomile (*Matricaria chamomilla* L.); Solanaceae such as black nightshade (*Solanum nigrum* L.), and jimsonweed (*Datura stramonium*); Amaranthaceae such as slender amaranth (*Amaranthus viridis* L.), and redroot pigweed (*Amaranthus retroflexus* L.); Polygonaceeae such as pale smartweed (*Polygonum lapathifolium* L.), ladysthumb (*Polygonum persicaria* L.), wild buckwheat (*Polygonum convolvulus* L.), and knotweed (*Polygonum aviculare* L.); Cruciferae such as flexuous bittercress (*Cardamine flexuosa* WITH.), shepherd's-purse (*Capsella bursa-pastoris* Medik.), and indian mustard (*Brassica juncea* Czern.); Convolvulaceae such as tall morningglory (*Ipomoea purpurea* L.), field bindweed (*Convolvulus arvensis* L.), and ivyleaf morningglory (*Ipomoea hederacea* Jacq.); Chenopodiaceae such as common lambsquarters (*Chenopodium album* L.), and mexican burningbush (*Kochia scoparia* Schrad.); Portulacaceae such as common purslane (*Portulaca oleracea* L.); Leguminosae such as sicklepod (*Cassia obtusifolia* L.); Caryophyllaceae such as common chickweed (*Stellaria media* L.); Labiatae such as henbit (*Lamium amplexicaule* L.); Rubiaceae such as catchweed (*Galium spurium* L.); Euphorbiaceae such as threeseeded copperleaf (*Acalypha australis* L.); and Commelinaceae such as common dayflower (*Commelina communis* L.).

Therefore, they can be effectively used for selectively controlling noxious weeds in cultivation of useful crops such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), rye (*Secale cereale* L.), oat (*Avenal sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawnqrass (*Zoysia japonica* stend), peanut (*Arachis hypogaea* L.), flax (*Linum usitatissimum* L.), tobacco (*Nicotiana tabacum* L.), and coffee (*Coffea* spp.). Particularly, the herbicidal composition of the present invention is effectively used for selectively controlling noxious weeds in cultivation of corn, wheat, sugar cane, and the like. Its application range extends to crop plant fields, orchards and plantations. And the herbicidal composition of the present invention can be effectively used for nonselectively controlling noxious weeds.

The herbicidal composition of the present invention can effectively be used to selectively control noxious weeds in cultivation of various transgenic plants. Examples of the transgenic plants include insect resistant transgenic plants, plant disease-resistant transgenic plants, transgenic plants regarding the plant constituents, and herbicide-resistant transgenic plants.

The herbicidal benzoylpyrazole compound may be applied in an amount of preferably from 5 to 1,000 g/ha, more preferably from 10 to 100 g/ha. It is particularly very useful as a herbicidal composition for corn fields, since it can control noxious weeds or inhibit their growth without impairing corn.

In the present invention, a herbicidal compound other than the herbicidal benzoylpyrazole compound may be mixed if desired, whereby more excellent effects or activity may be exhibited in some cases. For example, it may sometimes be possible to improve e.g. the range of the weeds to be controlled, the timing for the application of the herbicide or the herbicidal activities. The herbicidal benzoylpyrazole compound and another herbicidal compound may be individually prepared and mixed at the time of application, or they may be formulated together and applied. Such another herbicidal compound may suitably be selected from the following compound groups (1) to (11) (common names or test codes). Even when not specifically mentioned here, in a case where such compounds have salts, alkyl esters, structural isomers such as optical isomers etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, chlorflurenol-methyl, aminocyclopyrachlor, aminocyclopyrachlor-methyl or aminocyclopyrachlor-potassium.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton, trietazine or metobromuron; a triazine type such as simazine, atrazine, atratone, simetryn, prometryn, dimethametryn, hexazinone, metribuzin, terbuthylazine, cyanazine, ametryn, cybutryne, triaziflam, indaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chiomethoxyfen, bifenox, acifluorfen, acifluorfen-sodium, fomesafen, fomesafen-sodium, oxyfluorfen, lactofen, aclonifen, ethoxyfen-ethyl, fluoroglycofen-ethyl or fluoroglycofen; a cyclic imide type such as chlorphthalim, flumioxazin, flumiclorac, flumiclorac-pentyl, cinidon-ethyl, fluthiacet or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl, bencarbazone, halauxifen, tiafenacil or ethyl[3-(2-chloro-4-fluoro-5-(3-methyl-2,6-dioxo-4-trifluoromethyl-3,6-dihydro-2H-pyrimidin-1-yl)phenoxy)pyridin-2-yloxy]acetate.

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefuryltrione, bicyclopyrone, isoxaflutole, difenzoquat, difenzoquat-metilsulfate, isoxachlortole, benzobicyclon, picolinafen, beflubutamid, cyclopyrimorate, KUH-110 or a compound disclosed in the claim of WO2005118530.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, rimsulfuron, nicosulfuron, flazasulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron, metazosulfuron, iofensulfuron or a compound disclosed in the claim of EP0645386; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan; a sulfonylaminocarbonyltriazolinone type such as flucarbazone, flucarbazone-sodium, propoxycarbazone-sodium, propoxycarbazone or thiencarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium, cinmethylin or triafamone.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochlor or dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone, fenoxasulfone, dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid, nonanoic acid, fosamine, fosamine-ammonium, pinoxaden, ipfencarbazone, aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, methiozolin, etc.

(11) Those which are believed to exhibit herbicidal effects by being parasitic on plants, such as *Xanthomonas campestris, Epicoccosirus nematosorus, Epicoccosirus nematosperus, Exserohilurn monoseras* or *Drechsrela monoceras*.

In the present invention, in a case where the herbicidal benzoylpyrazole compound is formulated with various additives, or in a case where the herbicidal benzoylpyrazole compound and the activity-improving component are formulated together with various additives, it may be formulated into various formulations such as wettable powders, water dispersible granules, water-based suspensions, oil-based suspensions, gel formulation, emulsifiable concentrates, soluble concentrates, liquid formulation, emulsions, microemulsions, suspoemulsions and composite emulsions. The additives which can be used may be any additives so long as they are used in this technical field, and they may, for example, be a surfactant, a carrier, a solvent, a vegetable oil, a mineral oil, an anti-settling agent, a thickener, an anti-foaming agent, an anti-freezing agent, an antioxidant agent, an oil absorb agent, a gelling agent, a filler, a dispersion stabilizer, a safener, an anti-mold agent, a binder, a stabilizer, a disintegrator, a preservative agent and an inorganic ammonium salt. Specific examples of the additives include the following compounds. The herbicidal benzolypyrazole compound can be formulated in accordance with a conventional method in this technical field.

The surfactant may, for example, be an anionic surfactant such as a salt of fatty acid, a benzoate, an alkylsulfosuccinate, a dialkylsulfosuccinate, a polycarboxylate, a salt of alkyl sulfuric acid ester, an alkyl sulfate, an alkyl aryl sulfate, an alkyl diglycol ether sulfate, a salt of alcohol sulfuric acid ester, an alkyl sulfonate, an alkyl aryl sulfonate, an aryl sulfonate, a lignin sulfonate, an alkyl diphenyl ether disulfonate, a polystyrene sulfonate, a salt of alkyl phosphoric acid ester, an alkyl aryl phosphate, a styryl aryl phosphate, a salt of POE alkyl ether sulfuric acid ester, a POE alkyl aryl ether sulfate, a POE styryl aryl ether sulfate, a POE styryl aryl ether sulfonate, an ammonium salt of POE styryl aryl ether sulfate, a salt of POE alkyl aryl ether sulfuric acid ester, a POE alkyl ether phosphate, a salt of POE alkyl aryl phosphoric acid ester, a POE styryl aryl ether phosphoric acid ester or its salt, a salt of naphthalene suifonic acid condensed with formaldehyde, or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a POE alkyl ether, a POE aryl ether, a POE alkyl aryl ether, a POE styryl aryl ether, a POE glycol alkyl ether, a POE alkyl ester, a POE sorbitan alkyl ester, a POE sorbitol alkyl ester, a POE fatty acid ester, a POE sorbitan fatty acid ester, a POE sorbitol fatty acid ester, a POE glycerin fatty acid ester, POE hydrogenated castor oil, POE castor oil or a polyoxypropylene fatty acid ester; or a cationic surfactant such as an alkoxylated fatty amine, and they may be used as a mixture of two or more if desired.

The carrier or the filler may, for example, be diatomaceous earth, slaked lime, calcium carbonate, talc, white carbon, kaolin, bentonite, a mixture of kaolinite and sericite, clay, sodium carbonate, sodium bicarbonate, mirabilite, zeolite, starch, sodium chloride, ammonium phosphate, ammonium sulfate, ammonium chloride, sugar, urea, lactose or glucose, and they may be used as a mixture of two or more if desired.

The solvent may, for example, be water, solvent naphtha, paraffin, dioxane, acetone, isophorone, methyl isobutyl ketone, cyclohexane, dimethyl sulfoxide, dimethyl formamide, N-methyl-2-pyrolidone, an alcohol, acetic acid, butyric acid, isopropyl acetate, butyl acetate, alkylbenzene, alkylnaphthalene or a glycol. They may be used as a mixture of two or more if desired.

The vegetable oil may, for example, be olive oil, kapok oil, castor oil, papaya oil, camelia oil, coconut oil, sesame oil, corn oil, rice bran oil, peanut oil, cottonseed oil, soybean oil, rapeseed oil, linseed oil, tung oil, sunflower oil, safflower oil, a fatty acid derived from the above-described respective oils, or an alkyl ester of the fatty acid, and the mineral oil may, for example, be an aliphatic hydrocarbon such as liquid paraffin or paraffin petroleum, or an aromatic hydrocarbon such as an alkylbenzene or an alkylnaphthalene, and they may be used as a mixture of two or more if desired. The above-described fatty acid may, for example, be a $C_{12-22}$ saturated or unsaturated fatty acid such as lauric acid, palmitic acid, stearic acid, oleic acid, linoleic acid, linolenic acid, erucic acid or brassidic acid, and the alkyl ester thereof may be a $C_{1-18}$ linear or branched alkyl ester such as a methyl ester, a butyl ester, an isobutyl ester or an oleyl ester.

The anti-settling agent may, for example, be silica, organic bentonite (bentonite-alkylamino complex), bentonite, white carbon or aluminum magnesium silicate, and they may be used as a mixture of two or more if desired.

The thickener may, for example, be a heteropolysaccharide such as xanthan gum or guar gum, a water-soluble polymer such as polyvinyl alcohol, carboxymethylcellulose sodium salt or sodium alginate, or bentonite or white carbon, and they may be used as a mixture of two or more if desired.

The anti-foaming agent may, for example, be polydimethylsiloxane or acetylene alcohol, and they may be used as a mixture of two or more if desired.

The anti-freezing agent may, for example, be ethylene glycol, propylene glycol, glycerin or urea, and they may be used as a mixture of two or more if desired.

The oil absorb agent may, for example, be silicon dioxide, starch hydrolysate, kaolin, clay, talc, diatomaceous earth, artificial diatomaceous earth/lime, asbestos, a mixture of kaolinite and sericite, calcium silicate, precipitated calcium carbonate light, silicificated precipitated calcium carbonate light, acid clay, carbon black, natural earthy graphite, pearlite product, ultrafine aluminum oxide anhydrous particles, ultrafine titanium oxide particles, basic magnesium carbonate, magnesium aluminosilicate, a silica/alumina synthetic filler or magnesium silicate hydrate, and they may be used as a mixture of two or more if desired.

The gelling agent may, for example, be silica, organic attapulgite, clay, hydrogenated castor oil, a higher fatty acid ester, a higher alcohol, a salt of dialkylsulfosuccinic acid ester, a salt of benzoic acid, an alkyl sulfate, a mixture of a polyacrylic polymer or a polyacrylic copolymer and water, or 12-hydroxystearic acid, and they may be used as a mixture of two or more if desired.

The binder may, for example, be lignin sulfonate, xanthan gum, carboxymethylcellulose or starch, and they may be used as a mixture of two or more if desired.

The disintegrator may, for example, be an inorganic salt such as carboxymethyl cellulose calcium salt, ammonium sulfate, potassium chloride or magnesium chloride, or one having disintegrating effect among the above-mentioned surfactants, such as sodium lauryl sulfate, sodium dodecylbenzene sulfonate or ammonium polyacrylate, and they may be used as a mixture of two or more if desired.

The preservative agent may, for example, be formaldehyde, parachlorometaxylenol or 1,2-benzoisothiazolin-3-one, and they may be used as a mixture of two or more if desired.

In the above various formulations, the blend ratio of the respective components cannot be generally be defined, as it varies depending upon various conditions such as the type of the components, the type of the formulation, and the application site. For example, the herbicidal benzoylpyrazole compound is blended in a ratio of preferably from 0.1 to 95 parts by weight, more preferably from 2 to 85 parts by weight, and as the rest, the additives are blended in a ratio of preferably from 5 to 99.9 parts by weight, more preferably from 15 to 98 parts by weight. Further, in a case where the activity-improving component is blended in a ratio of preferably from 0.1 to 94.9 parts by weight, more preferably from 5 to 60 parts by weight if desired, and another herbicidal compound is blended in a ratio of preferably from 0.1 to 94.9 parts by weight, more preferably from 0.5 to 75 parts by weight if desired, the additives are blended as the rest, so that the total amount is 100 parts by weight. The blend ratios of the respective components in several formulations are mentioned below, however, the present invention is not limited to such specific formulations.

In the case of a water-based suspension, the herbicidal benzoylpyrazole compound is blended in a ratio of preferably from 0.1 to 60 parts by weight, more preferably from 2 to 50 parts by weight, the surfactant is blended in a ratio of preferably from 0.5 to 20 parts by weight, more preferably from 1 to 15 parts by weight, and as the rest, water is blended in a ratio of preferably from 25 to 99.4 parts by weight, more preferably from 30 to 97 parts by weight to prepare a water-based suspension. Further, in a case where the activity-improving component is blended in a ratio of preferably from 0.1 to 60 parts by weight, more preferably from 5 to 40 parts by weight if desired, another herbicidal compound is blended in a ratio of preferably from 0.1 to 60 parts by weight, more preferably from 0.5 to 30 parts by weight if desired, an anti-foaming agent is blended in a ratio of preferably from 0.05 to 3 parts by weight, more preferably from 0.1 to 1 part by weight if desired, an anti-freezing agent is blended in a ratio of preferably from 0.5 to 10 parts by weight, more preferably from 2 to 10 parts by weight if desired, an anti-settling agent is blended in a ratio of preferably from 0.1 to 5 parts by weight, more preferably from 0.5 to 3 parts by weight if desired, a thickener is blended in a ratio of preferably from 0.1 to 5 parts by weight, more preferably from 0.1 to 2 parts by weight if desired, and a preservative agent is blended in a ratio of preferably from 0.01 to 1 part by weight, more preferably from 0.05 to 0.2 part by weight if desired, water is blended as the rest so that the total amount is 100 parts by weight to prepare a water-based suspension.

In the case of an oil-based suspension, the herbicidal benzoylpyrazole compound is blended in a ratio of preferably from 0.1 to 40 parts by weight, more preferably from 2 to 35 parts by weight, the surfactant is blended in a ratio of preferably from 1 to 30 parts by weight, more preferably from 1 to 25 parts by weight, and as the rest, an oil, preferably a vegetable oil or a mineral oil is blended in a ratio of preferably from 10 to 98.9 parts by weight, more preferably from 20 to 97 parts by weight to prepare an oil-based suspension. Further, in a case where the activity-improving component is blended in a ratio of preferably from 0.1 to 80 parts by weight, more preferably from 5 to 60 parts by weight if desired, another herbicidal compound is blended in a ratio of preferably from 0.1 to 40 parts by weight, more preferably from 0.5 to 30 parts by weight if desired, and an anti-settling agent is blended in a ratio of preferably from 0.1 to 5 parts by weight, more preferably from 0.5 to 3 parts by weight if desired, a vegetable oil or a mineral oil is blended as the rest so that the total amount is 100 parts by weight to prepare an oil-based suspension.

In the case of a wettable powder, the herbicidal benzoylpyrazole compound is blended in a ratio of preferably from 0.1 to 95 parts by weight, more preferably from 5 to 85 parts by weight, the surfactant is blended in a ratio of preferably from 0.5 to 40 parts by weight, more preferably from 5 to 30 parts by weight, and as the rest, a carrier or a filler is blended in a ratio of preferably from 4.5 to 99.4 parts by weight, more preferably from 10 to 90 parts by weight to prepare a wettable powder. Further, in a case where the activity-improving component is blended in a ratio of preferably from 0.1 to 94.9 parts by weight, more preferably from 10 to 60 parts by weight if desired, another herbicidal compound is blended in a ratio of preferably from 0.1 to 94.9 parts by weight, more preferably from 0.5 to 75 parts by weight if desired, and an oil absorb agent is blended in a ratio of preferably from 1 to 90 parts by weight, more preferably from 1 to 50 parts by weight if desired, a carrier or a filler is blended as the rest so that the total amount is 100 parts by weight to prepare a wettable powder.

Preferred embodiments of the present invention will be described below, but the present invention is by no means restricted thereto.

1. A herbicidal composition comprising (1) 1-(1-ethyl-4-(3-(2-methoxyethoxy)-2-methyl-4-(methylsulfonyl)benzoyl)-1H-pyrazol-5-yloxy)ethyl methyl carbonate (the above compound No. 6) or its salt and (2) at least one compound selected from the group consisting of a POA sorbitan fatty acid ester, a POA fatty acid ester, a POA styryl aryl ether, a POA styryl aryl ether condensate and a POA alkyl ether sulfate (hereinafter referred to as an activity-improving component).

2. The herbicidal composition according to the above 1, wherein the activity-improving component is at least one compound selected from the group consisting of a POA sorbitan fatty acid ester and a POA fatty acid ester.

3. The herbicidal composition according to the above 1, wherein the activity-improving component is a POA sorbitan fatty acid ester.

4. The herbicidal composition according to the above 1, wherein the activity-improving component is a POA fatty acid ester.

5. A method for controlling undesired plants, which comprises applying (1) the above compound No. 6 or its salt and (2) the activity-improving component to the undesired plants or to a place where they grow.

6. The method according to the above 5, wherein the activity-improving component is at least one compound selected from the group consisting of a POA sorbitan fatty acid ester and a POA fatty acid ester.

7. The method according to the above 5, wherein the activity-improving component is a POA sorbitan fatty acid ester.

8. The method according to the above 5, wherein the activity-improving component is a POA fatty acid ester.

9. A method for improving the herbicidal activity of the compound No. 6 or its salt by using the activity-improving component.

10. The method according to the above 9, wherein the activity-improving component is at least one compound selected from the group consisting of a POA sorbitan fatty acid ester and a POA fatty acid ester.

11. The method according to the above 9, wherein the activity-improving component is a POA sorbitan fatty acid ester.

12. The method according to the above 9, wherein the activity-improving component is a POA fatty acid ester.

13. The herbicidal composition according to the above 3, the method according to the above 7, or the method according to the above 11, wherein the POA sorbitan fatty acid ester is at least one compound selected from the group consisting of POE sorbitan monolaurate, POE sorbitan dilaurate, POE sorbitan trilaurate, POE sorbitan monopalmitate, POE sorbitan dipalmitate, POE sorbitan tripalmitate, POE sorbitan monomyristate, POE sorbitan dimyristate, POE sorbitan trimyristate, POE sorbitan monostearate, POE sorbitan distearate, POE sorbitan tristearate, POE sorbitan monoisostearate, POE sorbitan diisostearate, POE sorbitan triisostearate, POE sorbitan monooleate, POE sorbitan dioleate and POE sorbitan trioleate.

14. The herbicidal composition according to the above 4, the method according to the above 8 or the method according to the above 12, wherein the POA fatty acid ester is at least one compound selected from the group consisting of POE monolaurate, POE dilaurate, POE monooleate, POE dioleate, POE monostearate, POE distearate, POE monoisostearate, POE diisostearate, POE monopalmitate, POE dipalmitate, POE monomyristate, POE dimyristate, POE di-2-ethylhexoate and POE dierucate.

15. The herbicidal composition according to the above 4, the method according to the above 8 or the method according to the above 12, wherein the POA fatty acid ester is POA di-fatty acid ester.

16. An oil-based suspension comprising (1) the above compound No. 6 or its salt, (2) the activity-improving component, (3) a surfactant and (4) a vegetable oil or a mineral oil.

17. The oil-based suspension according to the above 16, wherein the activity-improving component is at least one compound selected from the group consisting of a POA sorbitan fatty acid ester and a POA fatty acid ester.

18. The oil-based suspension according to the above 16, wherein the activity-improving component is a POA sorbitan fatty acid ester.

19. The oil-based suspension according to the above 16, wherein the activity-improving component is a POA fatty acid ester.

20. The oil-based suspension according to any one of the above 16 to 19, wherein (3) the surfactant is at least one surfactant selected from the group consisting of POE hydrogenated castor oil, POE styryl phenyl ether, a POE sorbitol fatty acid ester and a sorbitan fatty acid ester.

21. The oil-based suspension according to any one of the above 16 to 20, wherein (4) the vegetable oil or the mineral oil is a vegetable oil, a fatty acid derived from the vegetable oil or an alkyl ester of the fatty acid.

22. The oil-based suspension according to any one of the above 16 to 21, which contains (1) from 0.1 to 40 parts by weight of the above compound No. 6 or its salt, (2) from 0.1 to 80 parts by weight of the activity-improving component, (3) from 1 to 30 parts by weight of the surfactant, and (4) from 10 to 98.8 parts by weight of the vegetable oil or the mineral oil.

23. An oil-based suspension, which contains (1) from 0.1 to 40 parts by weight of the above compound No. 6 or its salt, (2) from 0.1 to 80 parts by weight of the activity-improving component, (3) from 1 to 30 parts by weight of a surfactant, (4) from 0.1 to 5 parts by weight of an anti-settling agent and (5) from 10 to 98.7 parts by weight of a vegetable oil or a mineral oil.

EXAMPLES

Now, the present invention will be described in further detail with reference to Examples. However, the present invention is by no means restricted to such specific Examples. Compound Nos. in Examples are compound Nos. in the above Table 1.

Example 1

(1) Compound No. 1, 2, 3, 4, 5, 6, 7, 8 or 9 (purity 99.6%): 36.26 parts by weight (2) Alkylnaphthalene sulfonate condensed with formaldehyde (tradename: Morwet D425 manufactured by AkzoNobel): 2.21 parts by weight (3) POE styryl phenyl ether phosphate potassium salt (tradename: Soprophor FLK/70 manufactured by Rhodia): 2.21 parts by weight (4) Aluminum magnesium silicate (tradename: Veegum R manufactured by Sanyo Chemical Industries, Ltd.): 0.88 part by weight (5) Propylene glycol: 6.19 parts by weight (6) Dimethylpolysiloxane (tradename: Silcolapse 432 manufactured by Bluestar Silicones): 0.35 part by weight (7) Xanthan gum (tradename: Rhodopol 23 manufactured by Rhodia): 0.09 part by weight (8) 1,2-Benzisothiazolin-3-one (tradename: Proxel GXL manufactured by Arch Chemicals, Inc.): 0.04 part by weight (9) Water: 51.77 parts by weight The above components are mixed and pulverized by a wet pulverizer for 5 minutes to prepare a water-based suspension. This is diluted with water together with the activity-improving component and applied.

Example 2

(1) Compound No. 1, 2, 3, 4, 5, 6, 7, 8 or 9 (purity: 99.6%): 36.26 parts by weight (2) Morwet D425 (tradename): 2.65 parts by weight (3) Ammonium POE styryl phenyl ether sulfonate (tradename: Soprophor 4D384 manufactured by Rhodia): 2.21 parts by weight (4) Veegum R (tradename): 0.88 part by weight (5) Propylene glycol: 6.19 parts by weight (6) Silcolapse 432 (tradename): 0.35 part by weight (7) Rhodopol 23 (tradename): 0.09 part by weight (8) Proxel GXL (tradename): 0.04 part by weight (9) Water: 51.33 parts by weight The above components are mixed and pulverized by a wet pulverizer for 5 minutes to prepare a water-based suspension. This is diluted with water together with the activity-improving component and applied.

Example 3

(1) Compound No. 1, 2, 3, 4, 5, 6, 7, 8 or 9 (purity: 99.6%): 36.26 parts by weight (2) Morwet D425 (tradename): 2.21 parts by weight (3) POE/polyoxypropylene block copolymer (tradename: Pluronic PE10300 manufactured by BASF): 2.21 parts by weight (4) Veegum R (tradename): 0.88 part by weight (5) Propylene glycol: 6.19 parts by weight (6) Silcolapse 432 (tradename): 0.35 part by weight (7) Rhodopol 23 (tradename): 0.09 part by weight (8) Proxel GXL (tradename): 0.04 part by weight (9) Water: 51.77 parts by weight The above components are mixed and pulverized by a wet pulverizer for 5 minutes to prepare a water-based suspension. This is diluted with water together with the activity-improving component and applied.

Example 4

(1) Compound No. 1, 2, 3, 4, 5, 6, 7, 8 or 9 (purity: 99.6%): 10.67 parts by weight (2) Mixture containing POE hydrogenated castor oil (tradename: Sorpol 3815A manufactured by TOHO Chemical Industry Co., Ltd.): 10.42 parts by weight (3) Organic bentonite (bentonite-alkylamino complex) (tradename: New D Orben manufactured by Shiraishi Kogyo Kaisha, Ltd.): 1.04 parts by weight (4) POE sorbitan fatty acid ester (tradename: Sorbon T-85 manufactured by TOHO Chemical Industry Co., Ltd.): 20.83 parts by weight (5) Methylated seed oil (tradename: AGNIQUE ME 18RD-F manufactured by BASF): 57.04 parts by weight The above components are mixed and pulverized by a wet pulverizer for 5 minutes to prepare an oil-based suspension. This is diluted with water and applied.

Example 5

(1) Compound No. 1, 2, 3, 4, 5, 6, 7, 8 or 9 (purity: 99.6%): 10.67 parts by weight (2) Sorbon T-85 (tradename): 31.25 parts by weight (3) New D Orben (tradename): 1.04 parts by weight (4) Isoparaffin (tradename: IP SOLVENT 1016 manufactured by Idemitsu Kosan Co., Ltd.): 57.04 parts by weight The above components are mixed and pulverized by a wet pulverizer for 5 minutes to prepare an oil-based suspension. This is diluted with water and applied.

Example 6

(1) Compound No. 1, 2, 3, 4, 5, 6, 7, 8 or 9 (purity: 99.6%): 31.25 parts by weight (2) Sorbon T-85 (tradename): 10.42 parts by weight (3) Silica (tradename: AEROSIL R972 manufactured by NIPPON AEROSIL CO., LTD.): 0.63 part by weight (4) POE styryl phenyl ether (tradename: Sorpol-19 manufactured by TOHO Chemical Industry Co., Ltd.): 10.42 parts by weight (5) IP SOLVENT 1016 (tradename): 47.28 parts by weight The above components are mixed and pulverized by a wet pulverizer for 5 minutes to prepare an oil-based suspension. This is diluted with water and applied.

Example 7

(1) Compound No. 1, 2, 3, 4, 5, 6, 7, 8 or 9 (purity: 99.6%): 10.67 parts by weight (2) Mixture containing POE sorbitol fatty acid ester (tradename: Sorpol 4300 manufactured by TOHO Chemical Industry Co., Ltd.): 10.42 parts by weight (3) New D Orben (tradename): 1.04 parts by weight (4) POE fatty acid ester (tradename: PEGNOL 24-0 manufactured by TOHO Chemical Industry Co., Ltd.): 52.08 parts by weight (5) Methylated seed oil (tradename: AGNIQUE ME 18RD-F manufactured by BASF): 25.79 parts by weight The above components are mixed and pulverized by a wet pulverizer for 5 minutes to prepare an oil-based suspension. This is diluted with water and applied.

Example 8

(1) Compound No. 1, 2, 3, 4, 5, 6, 7, 8 or 9 (purity: 99.6%): 10.67 parts by weight (2) Sorpol 3815A (tradename): 10.42 parts by weight (3) New D Orben (tradename): 1.04 parts by weight (4) Sorbon T-85 (tradename): 31.25 parts by weight (5) AGNIQUE ME 18RD-F (tradename): 46.62 parts by weight The above components are mixed and pulverized by a wet pulverizer for 5 minutes to prepare an oil-based suspension. This is diluted with water and applied.

Example 9

(1) Compound No. 1, 2, 3, 4, 5, 6, 7, 8 or 9 (purity: 99.6%): 10.67 parts by weight (2) Polycarboxylate (tradename: Geropon T/36 manufactured by Rhodia): 3 parts by weight (3) Alkylnaphthalene sulfonate (tradename: Supragil WP manufactured by Rhodia): 2 parts by weight (4) Alkyl naphthalene sulfonate condensed with formaldehyde (tradename: Supragil MNS/90 manufactured by Rhodia): 5 parts by weight (5) POE alkyl ether sulfate (tradename: HITENOL LA12 manufactured by DAI-ICHI KOGYO SEIYAKU CO., LTD.): 40 parts by weight (6) White carbon (tradename: Carplex #80 manufactured by Evonik Degussa Japan Co., Ltd.): 39.33 parts by weight HITENOL LA12 is adsorbed on Carplex #80, and mixed with the other components to prepare a wettable powder. This is diluted with water and applied.

Example 10

(1) Compound No. 6 (purity: 98%): 10.7 parts by weight
(2) Sorpol 4300 (tradename): 5 parts by weight
(3) New D Orben (tradename): 0.5 part by weight
(4) PEGNOL 24-O (tradename): 50 parts by weight
(5) AGNIQUE ME 18RD-F (tradename): 33.8 parts by weight The above components are mixed and pulverized by a wet pulverizer for 5 minutes to prepare an oil-based suspension. This is diluted with water and applied.

Example 11

(1) Compound No. 6 (purity: 97.3%): 3.0 parts by weight
(2) Nicosulfuron (purity: 94.2%): 3.2 parts by weight
(3) POE sorbitan fatty acid ester (tradename: Sorbon T-60 manufactured by
  TOHO Chemical Industry Co., Ltd.): 30.0 parts by weight
(4) Sorbitan fatty acid ester (tradename: Sorbon S-80 manufactured by TOHO Chemical Industry Co., Ltd.): 10.0 parts by weight
(5) New D Orben (tradename): 1.00 part by weight
(6) Urea: 1.5 parts by weight
(7) 2-Ethylhexanol: 5.0 parts by weight
(8) Corn oil: 46.30 parts by weight The above components are mixed and pulverized by a wet pulverizer for 5 minutes to prepare an oil-based suspension. This is diluted with water and applied.

Example 12

(1) Compound No. 6 (purity: 97.3%): 3.0 parts by weight
(2) Nicosulfuron (purity: 94.2%): 3.2 parts by weight
(3) POE fatty acid ester (tradename: CITHROL 4ML manufactured by CRODA): 30.0 parts by weight
(4) Sorbon S-80 (tradename): 10.0 parts by weight
(5) New D Orben (tradename): 1.00 part by weight
(6) Urea: 1.5 parts by weight
(7) 2-Ethylhexanol: 5.0 parts by weight
(8) Corn oil: 46.30 parts by weight The above components are mixed and pulverized by a wet pulverizer for 5 minutes to prepare an oil-based suspension. This is diluted with water and applied.

Now, Test Examples will be described. The activity-improving components used in Test Examples are as follows.

PEGNOL 24-O: POE(8) dioleate
RHEODOL TW-L120: POE(20) sorbitan monolaurate
Sorpol T-20: POE(19) tristyryl phenyl ether
Sorpol T-32: POE(30) tristyryl phenyl ether
Sorpol F-19: POE(26) distyryl phenyl ether condensate
HITENOL LA12: ammonium POE lauryl ether sulfate
HITENOL LA14: ammonium POE lauryl ether sulfate
AGNIQUE PEG600DO: POE dioleate
CITHROL 2DO: POE(4) dioleate
CITHROL 4ML: POE(8) monolaurate
NIKKOL MYL-10: POE(10) monolaurate
NIKKOL MYS-10: POE(10) monostearate
NIKKOL MYS-45: POE(45) monostearate
NIKKOL MYO-10: POE(10) monooleate
Sorbon T-40: POE(20) sorbitan monopalmitate
Sorbon T-60: POE(20) sorbitan monostearate
Sorbon T-80: POE(20) sorbitan monooleate
Sorbon T-85: POE sorbitan trioleate Test Example 1

Upland field soil was put into a 1/1,000,000 ha pot, and seeds of barnyardgrass (*Echinochloa crus-galli* L.) and seeds of velvetleaf (*Abutilon theophrasti* L.) were respectively sown and grown in a greenhouse. When the barnyardgrass reached 4.0 to 4.7-leaf stage and the velvetleaf reached 3.0 to 4.0-leaf stage, a prescribed amount (15 g a.i./ha) of a composition comprising compound No. 6 as an active ingredient prepared in accordance with Example 1 was diluted with water (containing 0.05 vol % of the activity-improving component) in an amount corresponding to 300 L/ha, and applied for foliar treatment. For comparison, a behenic acid monoethanolamide surfactant (tradename: Incromide manufactured by CRODA) was used at a concentration of 0.05 vol % instead of the activity-improving component of the present invention, and the composition was applied for foliar treatment similarly.

On the 25th day after treatment, the state of growth of the plants was visually observed to determine the growth inhibition rate (%)=0 (equivalent to the non-treated area) to 100 (complete kill), and the results as shown in Table 2 were obtained.

TABLE 2

| | Activity-improving component | Growth inhibition rate (%) | |
|---|---|---|---|
| | (surfactant, tradename) | Barnyardgrass | Velvetleaf |
| Present invention area | PEGNOL 24-O | — | 98 |
| | RHEODOL TW-L120 | 100 | 85 |
| | Sorpol T-20 | 97 | 83 |
| | Sorpol T-32 | 100 | 80 |
| | Sorpol F-19 | 100 | 85 |
| | HITENOL LA12 | 100 | 93 |
| Comparative area | Incromide | 70 | 70 |

Test Example 2

In accordance with the above Test Example 1, the effect on velvetleaf (*Abutilon theophrasti* L.) at 2.0 to 3.0-leaf stage was confirmed. For comparison, a methylated seed oil activity-strengthening agent (tradename: Destiny HO manufactured by agriliance) was used at a concentration of 0.5 vol %. On the 21st day after treatment, the growth inhibition rate (%) was determined in the same manner as in Test Example 1 and the results are shown in Table 3.

TABLE 3

| | Activity-improving component (surfactant, tradename) | Growth inhibition rate (%) Velvetleaf |
|---|---|---|
| Present invention area | PEGNOL 24-O | 83 |
| | AGNIQUE PEG600DO | 93 |
| | CITHROL 2DO | 85 |
| Comparative area | Destiny HC | 80 |

Test Example 3

In accordance with the above Test Example 1, the effect on velvetleaf (*Abutilon theophrasti* L.) at 3.3 to 3.8-leaf stage was confirmed. For comparison, methyl oleate (a mixture of methyl oleate: commercially available emulsifying agent=88:12) was used at a concentration of 0.05 vol %. The commercially available emulsifying agent used was a mixture of POE alkyl aryl ether, POE hydrogenated castor oil ether, a fatty acid derivative and sodium dialkylsulfosuccinate (tradename: Sorpol 3815K, manufactured by TOHO Chemical Industry Co., Ltd.). On the 21st day after treatment, the growth inhibition rate was determined in the same manner as in Test Example 1 and the results are shown in Table 4.

TABLE 4

| | Activity-improving component (surfactant, tradename) | Growth inhibition rate (%) Velvetleaf |
|---|---|---|
| Present invention area | PEGNOL 24-O | 65 |
| | AGNIQUE PEG600DO | 65 |
| | CITHROL 2DO | 65 |
| | NIKKOL MYL-10 | 68 |
| | NIKKOL MYS-10 | 68 |
| | NIKKOL MYS-45 | 63 |
| Comparative area | Methyl oleate | 58 |

Test Example 4

In accordance with the above Test Example 1, the effect on barnyardgrass (*Echinochloa crus-galli* L.) at 3.5 to 4.3-leaf stage was confirmed. For comparison, methyl oleate (the same as in Test Example 3) was used at a concentration of 0.05 vol %. On the 23rd day after treatment, the growth inhibition rate was determined in the same manner as in Test Example 1 and the results are shown in Table 5. Here, when no activity-improving component was added, the growth inhibition rate of barnyardgrass was 0%.

TABLE 5

| | Activity-improving component (surfactant, tradename) | Growth inhibition rate (%) Barnyardgrass |
|---|---|---|
| Present invention area | NIKKOL MYO-10 | 70 |
| | NIKKOL MYL-10 | 50 |
| Comparative area | Methyl oleate | 25 |

Test Example 5

Upland field soil was put into a 1/1,000,000 ha pot, and seeds of crabgrass (*Digitaria ciliaris* (Retz.) Koel.) were sown and grown in a greenhouse. When the crabgrass reached 3.6 to 4.2-leaf stage, a prescribed amount (30 g a.i./ha) of a composition comprising compound No. 6 as an active ingredient prepared in accordance with Example 1 was diluted with water (containing 0.05 vol % of the activity-improving component) in an amount corresponding to 300 L/ha, and applied for foliar treatment. For comparison, a polyoxyethylene octyl phenyl ether surfactant (tradename: KUSARINO manufactured by NIHON NOYAKU CO., Ltd.) or methyl oleate (the same as in Test Example 3) were used at a concentration of 0.05 vol % instead of the activity-improving component of the present invention, and each composition was applied similarly. On the 25th day after treatment, the growth inhibition rate was determined in the same manner as in Test Example 1 and the results are shown in Table 6.

TABLE 6

| | Activity-improving component (surfactant, tradename) | Growth inhibition rate (%) Crabgrass |
|---|---|---|
| Present invention area | CITHROL 4ML | 80 |
| | Sorbon T-40 | 78 |
| | Sorbon T-60 | 80 |
| | Sorbon T-80 | 97 |
| | Sorbon T-85 | 93 |
| | HITENOL LA-14 | 99 |
| Comparative area | KUSARINO | 45 |
| | Methyl oleate | 60 |

Test Example 6

Upland field soil was put into a 1/1,000,000 ha pot, and seeds of barnyardgrass (*Echinochloa crus-galli* L.) were sown and grown in a greenhouse. When the barnyardgrass reached 4.0 to 5.0-leaf stage, a prescribed amount (100 g a.i./ha) of a composition comprising compound No. 6 as an active ingredient prepared in accordance with Example 1 was diluted with water (containing 0.025 vol % of the activity-improving component) in an amount corresponding to 300 L/ha, and applied for foliar treatment. For comparison, KUSARINO (the same as in Test Example 5) was used at a concentration of 0.025 vol % instead of the activity-improving component of the present invention, and the composition was applied similarly. On the 21st day after treatment, the growth inhibition rate was determined in the same manner as in Test Example 1 and the results are shown in Table 7.

TABLE 7

| | Activity-improving component (surfactant, tradename) | Growth inhibition rate (%) Barnyardgrass |
|---|---|---|
| Present invention area | Sorbon T-60 | 94 |
| | HITENOL LA12 | 92 |
| Comparative area | KUSARINO | 30 |

Test Example 7

Upland field soil was put into a 1/1,000,000 ha pot, and seeds of velvetleaf (*Abutilon theophrasti* L.) were sown and grown in a greenhouse. When the velvetleaf reached 4.4 to 5.4-leaf stage, a prescribed amount (10 g a.i./ha) of a composition comprising compound No. 6 as an active ingredient prepared in accordance with Example 1 was diluted with water (containing 0.5 vol % of the activity-improving component) in an amount corresponding to 300 L/ha, and applied for foliar treatment. For comparison, KUSARINO (the same as in Test Example 5) was used at a concentration of 0.5 vol % instead of the activity-improving component of the present invention, and the composition was applied similarly. On the 22nd day after treatment, the growth inhibition rate was determined in the same manner as in Test Example 1 and the results are shown in Table 8.

TABLE 8

|  | Activity-improving component (surfactant, tradename) | Growth inhibition rate (%) Velvetleaf |
|---|---|---|
| Present invention area | Sorbon T-60 | 96 |
|  | HITENOL LA12 | 98 |
| Comparative area | KUSARINO | 90 |

Test Example 8

Upland field soil was put into a 1/1,000,000 ha pot, and seeds of barnyardgrass (*Echinochloa crus-galli* L.) and velvetleaf (*Abutilon theophrasti* L.) were sown and grown in a greenhouse. When the barnyardgrass reached 4.0 to 4.5-leaf stage and the velvetleaf reached 2.7 to 3.5-leaf stage, a prescribed amount (30 g a.i./ha) of an oil-based suspension comprising compound No. 6 as an active ingredient prepared in accordance with Example 10 was diluted with water in an amount corresponding to 300 L/ha, and applied for foliar treatment. On the 26th day after treatment, the state of growth of the barnyardgrass was visually observed, and on the 24th day after treatment, the state of growth of the velvetleaf was visually observed, to determine the growth inhibition rates in the same manner as in Test Example 1 and the results are shown in Table 9.

TABLE 9

|  | Activity-improving component | Growth inhibition rate (%) | |
|---|---|---|---|
| Ex. | (surfactant, tradename) | Barnyardgrass | Velvetleaf |
| 10 | PEGNOL 24-O | 95 | 83 |

Test Example 9

Upland field soil was put into a 1/1,000,000 ha pot, and seeds of corn (*Zea mays* L.) were sown and grown in a greenhouse. When the corn reached 3.8 to 4.5-leaf stage, a prescribed amount (30, 60 or 90 g a.i./ha) of an oil-based suspension comprising compound No. 6 as an active ingredient prepared in accordance with Example 10 was diluted with water in an amount corresponding to 300 L/ha, and applied for foliar treatment. On the 6th day after treatment, the growth inhibition rate was determined in the same manner as in Test Example 1 and the results are shown in Table 10.

TABLE 10

| Ex. | Activity-improving component (surfactant, tradename) | Dose (g a.i./ha) | Growth inhibition rate (%) Corn |
|---|---|---|---|
| 10 | PEGNOL 24-O | 30 | 0 |
|  |  | 60 | 0 |
|  |  | 90 | 3 |

Test Example 10

Upland field soil was put into a 1/1,000,000 ha pot, and seeds of crabgrass {P47051 02264045.000} (*Digitaria ciliaris* (Retz.) Koel.) and barnyardgrass (*Echinochloa crus-galli* L.) were sown and grown in a greenhouse. When the crabgrass reached 4.4 to 5.4-leaf stage and the barnyardgrass reached 4.0 to 5.1-leaf stage, prescribed amounts (30+30 g a.i./ha) of oil-based suspensions each comprising compound No. 6 and nicosulfuron as active ingredients, prepared in accordance with Examples 11 and 12, were diluted with water in an amount corresponding to 300 L/ha and applied for foliar treatment. On the 21st day after treatment, the growth inhibition rate was determined in the same manner as in Test Example 1 and the results are shown in Table 11.

TABLE 11

|  | Activity-improving component | Growth inhibition rate (%) | |
|---|---|---|---|
| Ex. | (surfactant, tradename) | Crabgrass | Barnyardgrass |
| 11 | Sorbon T-60 | 97 | 99 |
| 12 | CITHROL 4ML | 96 | 98 |

INDUSTRIAL APPLICABILITY

According to the present invention, a herbicidal composition having improved herbicidal activity can be provided.

The entire disclosure of Japanese Patent Application No. 2012-147798 filed on Jun. 29, 2012 including specification, claims and summary is incorporated herein by reference in its entirety.

The invention claimed is:

1. A herbicidal composition comprising (1) a benzoylpyrazole compound: 1- (1-ethyl-4- (3 - (2-methoxyethoxy)-2-methyl-4- (methylsulfonyl)benzoyl)- 1H-pyrazol-5-yloxy)ethyl methyl carbonate or its salt,
and (2) at least one compound selected from the group consisting of a polyoxyalkylene sorbitan fatty acid ester, a polyoxyalkylene fatty acid ester, a polyoxyalkylene styryl aryl ether, a polyoxyalkylene styryl aryl ether condensate and a polyoxyalkylene alkyl ether sulfate, and
wherein the mixing ratio of the benzoylpyrazole compound (1) and the compound (2) is from 1:0.75 to 1:150 by weight.

2. The herbicidal composition according to claim 1, wherein the compound (2) is at least one compound selected from the group consisting of a polyoxyalkylene sorbitan fatty acid ester and a polyoxyalkylene fatty acid ester.

3. The herbicidal composition according to claim 1, wherein the mixing ratio of the benzoylpyrazole compound (1) and the compound (2) is from 1:0.75 to 1:100 by weight.

4. A method for controlling undesired plants, which comprises applying (1) a benzoylpyrazole compound: 1-(1-ethyl-4-(3-(2-methoxyethoxy)-2-methyl-4-(methylsulfonyl)benzoyl)-1H-pyrazol-5-yloxy)ethyl methyl carbonate or its salt,
and (2) at least one compound selected from the group consisting of a polyoxyalkylene sorbitan fatty acid ester, a polyoxyalkylene fatty acid ester, a polyoxyalkylene styryl aryl ether, a polyoxyalkylene styryl aryl ether condensate and a polyoxyalkylene alkyl ether sulfate, to the undesired plants or to a place where they grow, and wherein the mixing ratio of the benzoylpyrazole compound (1) and the compound (2) is from 1:0.75 to 1:150 by weight.

5. The method according to claim 4, wherein the compound (2) is at least one compound selected from the group consisting of a polyoxyalkylene sorbitan fatty acid ester and a polyoxyalkylene fatty acid ester.

6. The method according to claim 4, wherein the mixing ratio of the benzoylpyrazole compound (1) to the compound (2) is from 1:0.75 to 1:100 by weight.

7. A method of improving the herbicidal activity of (1) a benzoylpyrazole compound: 1-(1-ethyl-4-(3-(2-methoxyethoxy)-2-methyl-4-(methylsulfonyl)benzoyl)-1H-pyrazol-5-yloxy)ethyl methyl carbonate or its salt, by using (2) at least one compound selected from the group consisting of a polyoxyalkylene sorbitan fatty acid ester, a polyoxyalkylene fatty acid ester, a polyoxyalkylene styryl aryl ether, a polyoxyalkylene styryl aryl ether condensate and a polyoxyalkylene alkyl ether sulfate, and wherein the mixing ratio of the benzoylpyrazole compound (1) and the compound (2) is from 1:0.75 to 1:150 by weight.

8. The method according to claim 7, wherein the compound (2) is at least one compound selected from the group consisting of a polyoxyalkylene sorbitan fatty acid ester and a polyoxyalkylene fatty acid ester.

9. The method according to claim 7, wherein the mixing ratio of the benzoylpyrazole compound (1) to the compound (2) is from 1:0.75 to 1:100by weight.

\* \* \* \* \*